United States Patent [19]

Linman et al.

[11] Patent Number: 4,681,793

[45] Date of Patent: Jul. 21, 1987

[54] NON-OCCLUDING, LIQUID-IMPERVIOUS, COMPOSITE BACKSHEET FOR ABSORPTIVE DEVICES

[75] Inventors: E. Kelly Linman; John J. Curro; Eugene Weinshenker, all of Cincinnati, Ohio

[73] Assignee: The Procter & Gamble Company, Cincinnati, Ohio

[21] Appl. No.: 740,084

[22] Filed: May 31, 1985

[51] Int. Cl.⁴ .............................................. B32B 3/10
[52] U.S. Cl. .................................. 428/138; 428/131; 428/156; 428/284; 428/913; 604/385 R
[58] Field of Search .................. 604/358, 378, 385 R; 428/913, 131, 134, 137, 138, 284, 156

[56] References Cited

U.S. PATENT DOCUMENTS

| D. 278,468 | 4/1985 | Trotman et al. | D92/1.1 |
|---|---|---|---|
| 3,426,754 | 2/1969 | Bierenbaum et al. | 128/156 |
| 3,881,489 | 5/1975 | Hartwell | 128/287 |
| 3,911,187 | 10/1975 | Raley | 428/180 |
| 3,929,135 | 12/1975 | Thompson | 128/287 |
| 3,957,414 | 5/1976 | Bussey, Jr. et al. | 425/384 |
| 3,965,906 | 6/1976 | Karami | 128/287 |
| 3,966,383 | 6/1976 | Bussey, Jr. et al. | 425/388 |

(List continued on next page.)

FOREIGN PATENT DOCUMENTS

| 101082A | 2/1984 | European Pat. Off. |
| 1104906 | 4/1984 | European Pat. Off. |
| 845826 | 8/1960 | United Kingdom |
| 1160625 | 8/1969 | United Kingdom |
| 2021479 | 12/1979 | United Kingdom |

OTHER PUBLICATIONS

U.S. patent application Ser. No. 740,145 filed 5/31/85 in the names of John J. Curro et al.
U.S. patent application Ser. No. 740,083 filed on 5/31/85, in the names of William R. Ouellette et al.
U.S. patent application Ser. No. 740,112 filed on 5/31/85 in the name of Hugh A. Thompson.
U.S. patent application Ser. No. 740,125 filed on 5/31/85 in the names of John J. Curro et al.
U.S. patent application Ser. No. 580,911 filed on 2/16/84 in the names of John J. Curro et al.

Primary Examiner—James J. Bell
Attorney, Agent, or Firm—E. Kelly Linman; John V. Gorman; Richard C. Witte

[57] ABSTRACT

A backing for an absorptive device such as a disposable diaper or a sanitary napkin, said backing comprising a combination of two layers. The first layer which does not contact the wearer's skin is preferably comprised of a liquid-impervious layer of polymeric film or the like. The second layer is also preferably comprised of a polymeric film which has been made pervious to liquid by providing a multiplicity of relatively small protuberances, each ending in an aperture, substantially across its entire surface. The apertured protuberances, which resemble a tiny volcano in cross-section, exhibit a soft, highly consumer preferred tactile impression which is sometimes characterized as "silky". In backsheets of the present invention, the second layer is oriented so that the tiny volcano-like cusps of the second layer constitute the exposed portion of the backsheet. This minimizes the area of contact between the backsheet and the wearer's skin. In a particularly preferred embodiment of the present invention, the second layer is macroscopically expanded to provide a three-dimensional pattern in its surface, thereby increasing the amount of stand-off between the wearer's skin and the liquid impermeable first layer of the composite backsheet. The tiny apertures in the second layer substantially prevent occlusion of the wearer's skin by providing circulation of air between the first liquid impervious layer of the backsheet of the wearer's skin. This effect is enhanced even further when the first layer is macroscopically expanded to enhance the amount of stand-off between the wearer's skin and the liquid impervious first layer. The reduced contact area and the enhanced air circulation between the backsheet and the wearer's skin reduce the tendency toward perspiration and sticking of the backsheet to the wearer's skin.

18 Claims, 4 Drawing Figures

U.S. PATENT DOCUMENTS

| | | | |
|---|---|---|---|
| 3,979,494 | 9/1976 | Ericson | 264/154 |
| 3,987,792 | 10/1976 | Hernandez et al. | 128/284 |
| 3,989,867 | 11/1976 | Sisson | 428/132 |
| 3,994,299 | 11/1976 | Karami | 128/287 |
| 4,041,951 | 8/1977 | Sanford | 128/287 |
| 4,151,240 | 4/1979 | Lucas et al. | 264/504 |
| 4,155,693 | 5/1979 | Raley | 425/363 |
| 4,157,237 | 6/1979 | Raley | 425/363 |
| 4,200,103 | 4/1980 | Black et al. | 128/290 |
| 4,226,828 | 10/1980 | Hall | 264/555 |
| 4,248,822 | 2/1981 | Schmidt | 264/154 |
| 4,321,924 | 3/1982 | Ahr | 128/287 |
| 4,323,069 | 4/1982 | Ahr et al. | 128/287 |
| 4,327,730 | 5/1982 | Sorensen | 128/287 |
| 4,341,216 | 7/1982 | Obenour | 128/287 |
| 4,341,217 | 7/1982 | Ferguson et al. | 128/290 |
| 4,342,314 | 8/1982 | Radel et al. | 128/287 |
| 4,343,848 | 8/1982 | Leonard, Jr. | 428/156 |
| 4,351,784 | 9/1982 | Thomas et al. | 264/22 |
| 4,395,215 | 7/1983 | Bishop | 425/290 |
| 4,397,644 | 8/1983 | Matthews et al. | 604/378 |
| 4,463,045 | 7/1984 | Ahr et al. | 428/131 |
| 4,477,502 | 10/1984 | O'Sullivan | 428/35 |
| 4,508,256 | 4/1985 | Radel et al. | 228/152 |
| 4,509,908 | 4/1985 | Mullane, Jr. | 425/290 |
| 4,518,643 | 5/1985 | Francis | 428/131 |
| 4,552,709 | 11/1985 | Koger et al. | 264/504 |
| 4,572,360 | 2/1986 | Lischka | 206/0.5 |
| 4,578,069 | 3/1986 | Whitehead et al. | 604/370 |

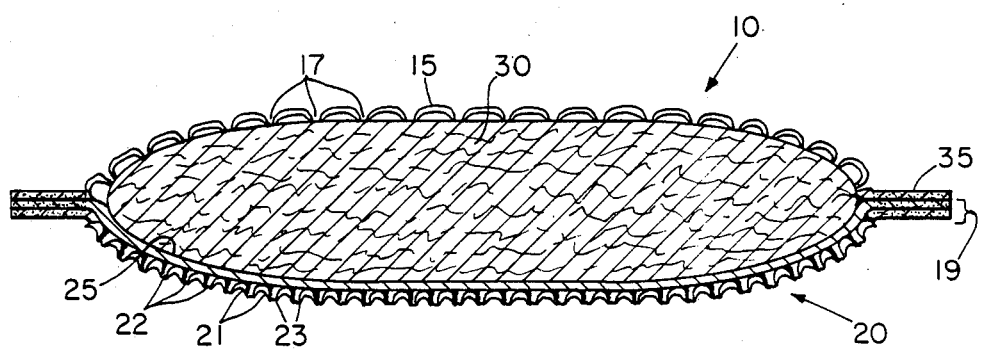

NON-OCCLUDING, LIQUID-IMPERVIOUS, COMPOSITE BACKSHEET FOR ABSORPTIVE DEVICES

FIELD OF THE INVENTION

The present invention relates generally to absorptive devices such as disposable diapers, sanitary napkins, disposable bedpads, incontinent pads, and the like.

The present invention has particular relation to a backing for such devices which exhibits a highly desirable tactile impression on its exposed surface, which prevents transmission of liquids absorbed within the absorptive device through the back side of the absorptive device, yet which improves wearer comfort by substantially preventing occlusion of the wearer's skin by those portions of the backsheet which come in contact therewith.

BACKGROUND OF THE INVENTION

Absorptive devices, such as diapers, sanitary napkins, disposable bedpads, incontinent pads, and the like are well known. These device are used to absorb liquid from the human body and retain that liquid, It is also known to cover the exterior of these devices with a flexible, plastic sheet to prevent the liquid absorbed from striking through the absorptive device and soiling other adjacent clothing, such as bedding and wearing apparel. Although such waterproof plastic sheets of the prior art are highly effective in preventing strike-through and help contain the liquid within the absorptive device, they also tend to be uncomfortable to wear. Accordingly, numerous prior art attempts have been made to provide breatheable backsheets for such absorptive devices, i.e., backsheets which are resistant to the passage of liquid moisture, but which are, at least to a degree, pervious to the passage of gases and vapors. The purpose of such prior art breatheable backsheets is to provide communication between the interior of the absorptive device and the exterior of the absorptive device, thus permitting evaporation of the absorbed liquids to the atmosphere and air circulation between the interior and exterior of the absorptive device.

Exemplary of such prior art absorptive devices employing breatheable backsheets are commonly assigned U.S. Pat. No. 3,989,867 issued to Sisson on Nov. 2, 1976; U.S. Pat. No. 3,156,242 issued to Crow, Jr on Nov. 10, 1964; U.S. Pat. No. 2,119,610 issued to Tasker on June 7, 1938; U.S. Pat. No. 3,439,678 issued to Thomas on Apr. 22, 1969; and commonly assigned U.S. Pat. No. 4,341,216 issued to Obenour on July 27, 1982, all of said patents being hereby incorporated herein by reference.

The aforementioned commonly assigned patent to Obenour discloses a disposable diaper provided with a two-element breatheable backsheet. The two elements are a vapor-pervious, relatively liquid-impervious outer sheet and a liquid-impervious inner panel. The inner panel is placed between the outer sheet and an absorbent core of the device in the crotch region of the disposable diaper. The relatively liquid-impervious outer panel disclosed by Obenour preferably comprises a polymeric film exhibiting a pattern of tapered capillaries as described in commonly assigned U.S. Pat. No. 3,929,135 issued to Thompson on Dec. 30, 1975. The outer panel is oriented in a direction such that the direction of relative liquid-impermeability is from the absorbent core to the exterior surface of the diaper. In the illustrated embodiment, this means that the apices of the tapered capillaries in the outer sheet are oriented in the direction of the absorbent core.

As with the earlier prior art structures, the primary thrust of Obenour is to permit breatheability between the moist absorptive core of the device and the atmosphere surrounding the exposed backsheet of the disposable diaper.

Because of the wide range of conditions experienced in use, absorbent devices of the prior art employing breatheable backsheets which permit limited communication between the absorptive element and the atmosphere surrounding the backsheet have not always functioned in the intended manner. For example, when such devices are subjected to higher than normal pressures due to movements or actions of the wearer, liquid may be discharged through the breatheable backsheet, thereby wetting the surrounding garments of the wearer.

An alternative prior art approach to improve wearer comfort yet preserve liquid impermeability between the absorptive element and the surrounding atmosphere has involved adding an additional wearer-contacting layer outside a moisture impermeable backing layer used to restrain the liquid. One such structure is disclosed in U.S. Pat. No. 4,200,103 issued to Black et al. on Apr. 29, 1980, which is hereby incorporated herein by reference.

The patent to Black et al. discloses an absorbent product for absorbing and retaining body fluids. It has a body facing side and a garment facing side and comprises an elongated, planar absorbent pad. The pad is enveloped in a generally rectangular, menstrual fluid-pervious wrapper with the longitudinal edges of the wrapper overlapping on the garment facing side of the product. A generally rectangular menstrual fluid-impervious barrier sheet is sandwiched between the wrapper and the pad. The barrier sheet overlies the garment facing side of the pad and at least the longitudinal side edges of the pad. At least two menstrual barrier seal lines are provided extending longitudinally with the product and sealing the longitudinal edge portions of the barrier sheet to the cover. The longitudinal seals are intended to prevent menstrual fluid from transferring, either by wicking or by seeping, across the seal line, while the fluid-impervious barrier sheet prevents strike-through of any absorbed fluids. In a particularly preferred embodiment of the Black et al. invention a pocket is formed between the barrier sheet and the overlying wrapper. According to Black et al., the area in this pocket is open to free circulation of moisture vapor and air on both the inside and the outside surfaces of the wrapper, whereby perspiration deposited on the longitudinal edges of the pad can be evaporated and removed from the product before causing user skin irritation.

The fluid-pervious wrapper of Black et al., in a preferred embodiment, is comprised of a substantially planar fibrous material which, according to Black et al., is prevented from wicking menstrual fluid to the outermost surface of the pad by the longitudinal barrier seals. When the pad of Black et al. is subjected to pressure, the wearer's skin causes the outermost wrapper to make contact with the underlying fluid-impervious barrier layer. Thus, in situations where the wrapper is subjected to continuous pressure, the pocket formed between the wrapper and the barrier layer will be non-functional in those areas subject to the continuous pressure, i.e., any air circulation between that portion of the wearer's body applying the pressure and the barrier layer must be provided through the substantially planar wrapper material. If the substantially planar fibrous wrapper material disclosed by Black et al. does not provide sufficient separation between the wearer's skin and the barrier layer of the pad to permit significant air circulation to occur between the wearer's skin and the barrier layer, this may result in wearer perspiration at the interface, with consequent wearer discomfort.

OBJECTS OF THE INVENTION

Accordingly, it is an object of the present invention to provide a composite backsheet comprising an outermost liquid-pervious wearer contacting layer and an innermost substantially liquid-impervious barrier layer, said composite backsheet being suitable for use on an absorptive device wherein the ability to provide air circulation between the wearer's skin and the liquid-impervious barrier layer of said composite backsheet is not dependant upon the formation of a pocket between the wearer contacting layer and the barrier layer.

It is another object of the present invention to provide a composite backsheet having a resilient, non-wicking polymeric exterior layer which can provide sustained air circulation between the wearer's skin and the underlying barrier layer, even when the absorbent device on which the backsheet is employed is subjected to normal pressures caused by the wearer's body movements.

It is another object of the present invention to provide such a composite backsheet having a wearer contacting surface which is generally consumer preferred when compared to prior art woven and nonwoven materials typically used in contact with the wearer's skin.

It is still another object of the present invention to provide a composite backsheet having a wearer contacting polymeric layer exhibiting a multiplicity of tiny apertured protuberances which minimize contact and frictional forces with the wearer's skin when there is relative movement between the backsheet and the wearer's skin, thereby minimizing the sensation of stickiness which often results when a backsheet does not readily move relative to the wearer's skin.

It is still another object of the present invention to provide a composite backsheet which does not generate a rustling noise upon movement by the wearer, thereby avoiding possible embarrassment to the wearer.

It is still another object of the present invention to provide methods for making such composite backsheets.

DISCLOSURE OF THE INVENTION

In a particularly preferred embodiment, the present invention comprises an absorptive element provided with a composite backsheet which is liquid-impervious, yet aesthetically and tactually pleasing. The composite backsheet preferably comprises a first outermost polymeric web having a multiplicity of small resilient protuberances, each having a volcano-shaped aperture at its apex. The polymeric web is oriented so that the protuberances face outwardly, thereby placing the volcano-like apertures in contact with the wearer's skin. A second interior layer comprised of substantially liquid-impervious material, such as another layer of polymeric film, prevents liquid absorbed within the absorptive device from penetrating the composite backsheet. The interior liquid-impervious layer may, if desired, be vapor-pervious, but this is not a requirement of the present invention. Those portions of the composite backsheet which do come in contact with the wearer's skin are non-occluding, since air circulation may readily occur between the outermost and innermost layers comprising the backsheet. In addition, because the surface area of the outermost web in contact with the skin is very small, there is little tendency for sticking to occur between the outermost layer and the wearer's skin when relative movement occurs between the two. As a result, composite backsheets of the present invention are generally perceived as non-sticky, i.e., there is very little tendency for the backsheet to stick to the skin and stretch the skin when movement of the wearer's body occurs relative to the backsheet of the absorptive device. It is believed that the tiny volcano-like apertures exhibit tiny feathered edges which tend to glide easily across the surface of the skin rather than sticking to it, thereby substantially eliminating the sticky feeling which normally results when the wearer's body undergoes movement relative to prior art polymeric webs.

Quite unexpectedly, it has also been learned that composite backsheets of the present invention do not generate the rustling sounds typically generated by unapertured polymeric backsheets of the prior art. This may be of considerable importance in products, such as adult incontinent briefs, where these rustling sounds can cause considerable embarassment to the wearer.

In a particularly preferred embodiment of the present invention, the innermost substantially liquid-impervious layer is comprised of a very thin polymeric membrane which prevents transmission of liquid, yet which is sufficiently soft and compliant that it does not create noise upon movement of the wearer's body. However, the substantially liquid-impervious layer may, if desired, be vapor-pervious. This layer may be secured either to or beneath the finely apertured outermost polymeric layer of the composite backsheet. In yet other embodiments of the present invention it may take the form of a substantially continuous coating applied to that surface of the finely apertured web which is opposite the volcano-like cusps.

Thus, backsheets of the present invention provide the highly desirable liquid-impervious properties characteristic of prior art polymeric film backsheets, but in combination with desirable tactile and aesthetic properties previously associated only with fibrous woven and nonwoven structures. In addition, composite backsheets of the present invention provide improved wearer comfort at points of contact without creating a noise problem which can often cause embarrassment to the wearer.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

FIG. 2 is a simplified cross-section of the sanitary napkin shown in FIG. 1 taken along section line 2—2 of FIG. 1;

DETAILED DESCRIPTION OF THE INVENTION

Figure 1:
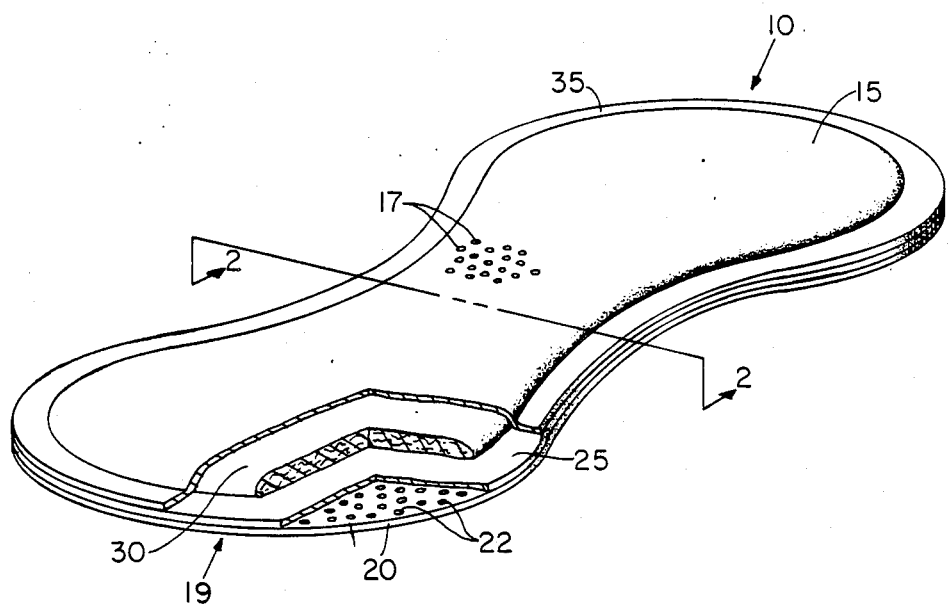
FIG. 1 is a simplified perspective view of a sanitary napkin employing a composite backsheet of the present invention.

In FIG. 1 there is shown a simplified view of a sanitary napkin 10 employing a composite backsheet 19 of the present invention. It should be understood that although the absorbent device described in detail herein is in the form of a sanitary napkin, the general principles of the present invention and its application to other absorbent devices or articles of apparel will be readily appreciated by those skilled in the art. In addition, the term "backsheet" is not intended to limit to a particular surface of the absorbent device. For example, the edges of the backsheet may, in certain instances be folded over and form a part of the face of the absorbent device, such as in a disposable diaper waistband, a disposable diaper legband or the like. Accordingly, its use as a particularly preferred backsheet material in a sanitary napkin is in no way intended to limit the present invention, the scope of which is fully described in the appended claims.

The sanitary napkin 10 shown generally in FIG. 1 is of a substantially hourglass shape to facilitate placement between the wearer's legs without causing distortion. Sanitary napkins of the type generally shown in FIG. 1 are often utilized as panty liners, and may be secured to the wearer's undergarments by means well known, such as, for example, a pressure sensitive adhesive tape (not shown) on the lowermost surface of the napkin. The sanitary napkin 10 preferably has a fluid-pervious topsheet 15 which, ideally, permits menses or other body fluids deposited on the uppermost surface of the structure to pass through the topsheet 15 and be retained by the absorbent element 30 lying beneath the topsheet. One particularly preferred topsheet material is comprised of a macroscopically expanded, three-dimensional polymeric web exhibiting a fiber-like appearance and tactile impression and having a multiplicity of capillary networks 17, each defined by a multiplicity of interconnected fiber-like elements. Structures of this general type are disclosed in commonly assigned U.S. Pat. No. 4,342,314 issued to Radel and Thompson on Aug. 3, 1982, said patent being hereby incorporated herein by reference. It will of course be understood that the particular type of topsheet is non-critical to the practice of the present invention, and may be readily formed of more conventional materials such as woven and nonwoven fibrous materials.

Absorbent element 30 may be comprised of any of the known absorbent materials, such as airlaid comminuted woodpulp fibers, commonly known as airfelt. Alternatively, absorbent element 30 may be comprised of plies of tissue paper, absorbent foam, or combinations of any of the aforementioned materials. The exact composition and construction of absorbent element 30 is also non-critical to the practice of the present invention.

In the embodiment shown in FIG. 1, absorbent element 30 is preferably of an hourglass shape. In a particularly preferred embodiment the periphery of absorbent element 30 is coextensive with the border of the topsheet 15. Beneath absorbent element 30 there is preferably provided a liquid-impervious composite backsheet 19 of the present invention. As can be seen in FIG. 1 and the cross-section of FIG. 2, composite backsheet 19 is comprised of an innermost layer 25 and an outermost layer 20. As can also be observed from FIGS. 1 and 2, the layers 20, 25 of composite backsheet 19, the intermediate edges of absorbent element 30 and topsheet 15 are secured to one another in a seal area 35 which forms the perimeter about the sanitary napkin 10. The bonded seal area 35 may be formed with or without the peripheral edges of absorbent element 30 being secured between the layers. Seal area 35 may be continuously bonded or spot bonded at random or predetermined intervals about the perimeter of napkin. Any suitable means well known in the art may be utilized to secure the various layers to one another, including, for example only, the use of relatively pliable adhesives intermediate the various layers. It is, of course, generally desirable that the edges of the seal area 35 remain soft so as not to cause chafing of the wearer's skin.

Because layers 20 and 25 are secured in superposed relation about the periphery of the sanitary napkin 10, it is not necessary that layers 20 and 25 be secured to one another at other locations along the lowermost surface of the napkin.

In a particularly preferred embodiment, innermost layer 25 of composite backsheet 19 is preferably comprised of a substantially liquid and vapor-impervious polymeric film such as polyethylene, preferably having a thickness between about 0.0002 inches and about 0.0008 inches. For extremely thin films, it may be desirable to extrusion coat the innermost layer onto the outermost apertured layer 20, particularly if the operation is to be carried out at high speed. It is also feasible to employ a substantially liquid-impervious, but vapor-pervious material in practicing the present invention. One such material is a porous polytetrafluorethylene web such as PLASTOLON available from Garlock, Inc. of Newtown, Pa. However, such liquid-impervious, vapor pervious materials are generally more expensive than liquid and vapor-impervious polymeric films.

Since it is normally not necessary for the liquid-impervious layer 25 to resist significant mechanical forces such as tension applied to the absorbent device, this material is normally chosen to be as thin as practical and as compliant as possible so that its presence does not generate noise whenever the wearer's body undergoes movement. Materials of low modulus are generally preferred, since they normally tend to be less noisy.

The outermost layer of the composite backsheet 19 preferably comprises a second layer of polymeric film exhibiting a multiplicity of relatively small, resilient protuberances 21, each exhibiting a tiny aperture 22 at its apex. As can be seen in the cross-section of FIG. 2, layer 20 is oriented so that the protuberances face outwardly away from the moisture impervious layer 25. As a result, the tiny apertures 22 at the peaks of the protuberances 21 have small volcano-shaped cusps 23 which may contact the wearer's skin when the sanitary napkin 10 is placed in use. The protuberances 21 may be formed by subjecting a substantially planar polymeric film to a fluid pressure differential while supported on a fine-scale forming structure, such as an 80 filament per inch × 80 filament per inch woven wire mesh comprised of filaments having a diameter of 7 mils. The apertured protuberances thus formed correspond to the interstices formed between intersecting filaments. To provide the visual and tactile benefits described herein it is generally preferred to use wire mesh counts of about 80 per inch×80 per inch or greater. As the mesh count increases, the filament diameter preferably decreases. More specific details as to particularly preferred size and spacing criteria for the multiplicity of protuberances are provided in the commonly assigned U.S. Patent Application of John J. Curro and E. Kelly Linman, entitled MICROAPERTURED POLYMERIC WEB EXHIBITING SOFT AND SILKY TACTILE IMPRESSION, Ser. No. 740,125, concurrently filed herewith, issued on Dec. 16, 1986 as U.S. Pat. No. 4,629,643, and hereby incorporated herein by reference.

While it is recognized that the backsheet of an absorbent device such as a sanitary napkin is normally not intended for extensive contact with the wearer's skin, it is significant to note that the exterior surface of the absorbent device often comes in contact with the wearer's skin when the device is placed in service. In particular, when a sanitary napkin is worn by an adult female, the exterior surfaces of the pad may conform to the pelvic area of the user such that the innermost surfaces of the thighs may make substantial contact with the outermost surface of the pad. This condition is generally illustrated in the cross-sectional schematic of FIG. 3, which discloses an alternative sanitary napkin embodiment 10' in use.

Similar skin contacting situations exist in circumstances involving incontinent adult briefs, baby diapers, and related structures wherein the backsheet material may be caused to come into contact with the wearer's skin to aid in establishing a seal to prevent leakage over the edges of the absorbent device.

While not wishing to be bound, it is believed that the nature of the contact between a composite backsheet of the present invention and the wearer's skin causes the wearer to perceive such absorbent devices as more comfortable and non-sticky. In particular, the tiny volcano-like cusps 23 located at the apex of each protuberance 21 have a very small contact area with the user's skin. Since the outermost web is resilient, the protuberances 21 tend to spring-back and restore air circulation to the skin wherever any compressive loads which are sufficient to temporarily collapse the protuberances are removed therefrom. By way of contrast, unapertured, non-resilient plastic backsheets of the prior art tend to exhibit a large contact area with the wearer's skin. Because there is a tendency for the large contact areas of a polymeric film to occlude the skin, thereby causing perspiration and consequent sticking of the skin to such prior art backsheets, relative movement of the wearer's body and the backsheet tends to stretch the wearer's skin when the wearer attempts to move. Furthermore, since most such webs are substantially planar and lack resilience, there is no tendency for them to separate from the wearer's skin once contact is established, at least until the wearer moves. It is believed that the adverse "sticky" comments often heard in connection with liquid-impervious prior art backsheets is due to the aforementioned tendency of the adhered skin and backsheet material to stick to one another when relative movement between the two surfaces occurs. This relative movement stretches the skin when the wearer's body moves sufficiently to cause separation between the affected portion of the wearer's body and the portion of the backsheet to which it is temporarily adhered. It is believed that this is one of the primary reasons such unapertured polymeric backsheets of the prior art produce a negative consumer reaction.

An additional benefit afforded by Applicants' composite backsheet 19 is that the relatively small volcano-like cusps 23 associated with apertures 22 do not significantly occlude the wearer's skin. The pattern of protuberances 21 allows air to continually circulate between the innermost layer 25 and the exterior layer 20 of the composite backsheet 19. Unlike prior art structures, such as those disclosed in the aforementioned patent to Black et al., this continual circulation of air is not dependent upon the formation of a pocket or any other structural member intermediate innermost liquid-impervious layer 25 and exterior apertured layer 20. Accordingly, it is independent of end product configuration.

Because of the improved air circulation it is believed that there is less tendency for the user's skin to perspire. It is further believed that the reduced contact area and the reduced tendency to cause perspiration both tend to minimize sticking of the wearer's skin to the backsheet. Consequently relative movement between the wearer's skin and composite backsheets of the present invention has a much lesser tendency to stretch the wearer's skin.

Figure 2A:
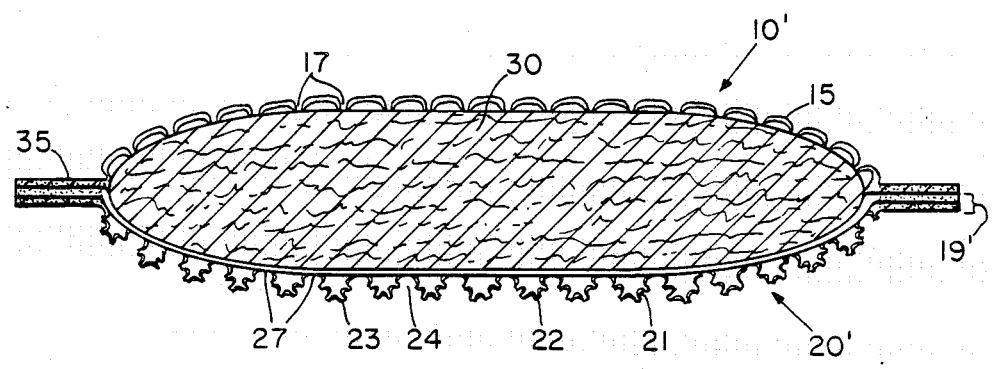
FIG. 2A is a simplified cross-section of an alternative sanitary napkin of the type generally shown in FIG. 1, also taken at a point corresponding to that of section line 2—2 of FIG. 1.

Another preferred embodiment of a sanitary napkin 10' of the present invention is shown in the cross-section of FIG. 2A. The sanitary napkin 10' shown in FIG. 2A is in most respects similar to the sanitary napkin 10 shown in FIG. 2 with the exception that the composite backsheet 19' of the present invention employs a macroscopically expanded, three-dimensional outermost layer 20' rather than a substantially planar outermost layer 20. Outermost layer 20' is generally similar to outermost layer 20 with the exception that is has been macroscopically expanded so as to exhibit a multiplicity of debossments 24 which increase the overall caliper of outermost layer 20'. If desired, the debossments 24 may also be formed with macroscopic cross-section apertures 27 at the end of each debossment 24. In the web embodiment 20' shown in FIGS. 2 and 3 protuberances 21, including tiny apertures 22 and volcano-like cusps 23 located at their apices, are present substantially uniformly across the surface of the macroscopically expanded, three-dimensional web 20'. Debossments 24 in layer 20' of composite backsheet 19' provide a three-dimensional macroscopic cross-section to the web which imparts an even greater feeling of resilience to web 20' when the exterior surface of sanitary napkin 10' is contacted by the wearer. In addition, due to the greater overall caliper of macroscopically expanded three-dimensional layer 20' and the presence of macroscopic cross-section apertures 27 at the ends of debossments 24, there is even more room for air to circulate intermediate liquid-impervious layer 25 and outermost layer 20'. This is illustrated with particular clarity by the arrows "A" shown in the cross-section of FIG. 3, which discloses a sanitary napkin 10' of the type disclosed in FIG. 2A in use.

Figure 3:
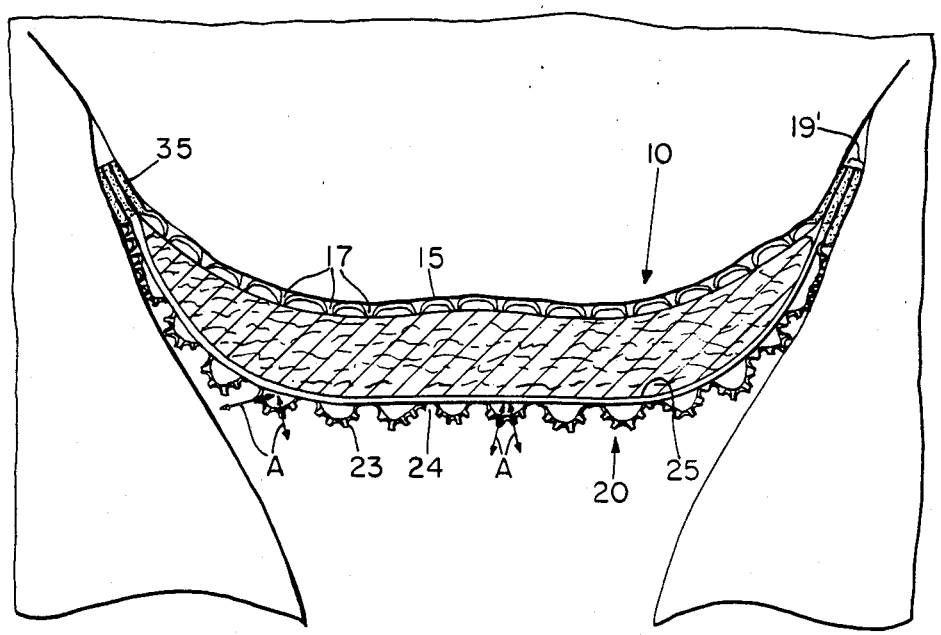
FIG. 3 is a simplified cross-sectional illustration generally similar to that of FIG. 2A, but showing the conformation of the sanitary napkin to the wearer's pelvic area and the type of contact established between the innermost surface of the wearer's thighs and the exterior surface of a composite backsheet of the present invention.

As can be seen in FIG. 3, even when the wearer's thighs exert pressure upon the resilient portions of exterior layer 20' with which they come in contact, the tiny protuberances 21 ending in apertures 22 help to prevent complete occlusion of the wearer's skin. Furthermore, when the wearer's body moves, as by walking, those portions of exterior layer 20' which contact the wearer's thighs move readily across the surface of the skin without sticking because of the presence of the tiny volcano-like cusps 23 formed about each tiny aperture 22.

Thus, while prior art techniques have for the most part, attempted to solve the "stickiness" problem by simply providing breatheable backsheets to resist the transmission of liquid, but permit vapors to pass through the backsheet from the absorbent element, it is believed that composite backsheets of the present invention solve many of the problems previously attributed to the lack of breatheability between the absorbent element and the surrounding atmosphere in a novel and unobvious manner. In particular, the solution provided by the present invention retains the security associated with liquid-impervious backsheets of the prior art. However, it eliminates the negative consumer reaction typically produced by such prior art backsheets by simultaneously eliminating the "stickiness" problem and providing visually and tactually preferred appearance and texture on the exterior surface of the backsheet.

Particularly preferred methods for making exterior layers 20 and 20' of composite backsheets 19 and 19', respectively, are disclosed in FIG. 1 of the commonly assigned U.S. Patent Application of John J. Curro, James C. Baird, Donald L. Gerth, George M. Vernon and E. Kelly Linman entitled MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES, Ser. No. 740,145, concurrently filed herewith issued on Sept. 2, 1986 as U.S. Pat. No. 4,609,518, and hereby incorporated herein by reference. Finely apertured webs, such as web 20, may be formed by subjecting a substantially planar web of polymeric film to only the first stage of the multi-stage forming process therein disclosed. Alternatively, finely apertured and macroscopically expanded, three-dimensional webs, such as web 20', may be formed by subjecting the polymeric film to both stages of the multi-stage process disclosed in FIG. 1 of the aforementioned commonly assigned U.S. Patent Application of John J. Curro, James C. Baird, Donald L. Gerth, George M. Vernon and E. Kelly Linman entitled MULTI-PHASE PROCESS FOR DEBOSSING AND PERFORATNG A POLYMERIC WEB TO COINCIDE WITH THE IMAGE OF ONE OR MORE THREE-DIMENSIONAL FORMING STRUCTURES, Ser. No. 740,145 issued on Sept. 2, 1986 as U.S. Pat. No. 4,609,518. Particularly preferred characteristics for wearer contacting webs such as 20 and 20' are described in detail in the commonly assigned U.S. Patent Application of John J. Curro and E. Kelly Linman, entitled MICROAPERTURED POLYMERIC WEB EXHIBITING SOFT AND SILKY TACTILE IMPRESSION, Ser. No. 740,125, concurrently filed herewith, issued on Dec. 16, 1986 as U.S. Pat. No. 4,629,643, and incorporated herein by reference.

As pointed out earlier herein composite backsheets of the present invention may be comprised of wearer contacting exterior and interior barrier layers which are merely secured in superposed relation to one another in the finished product or they may be bonded to one another in either random or uniform fashion. Alternatively the barrier layer may actually be applied to the exterior web as an extrusion or a coating and, if necessary, cured in place, e.g., as by an electron beam. For example, an extruder, such as a National Rubber Machinery Co. Pacemaker III (NRM Process Systems, Columbiana, Ohio) could be used to cast either a thin film (e.g., about 0.0002 inches in thickness) of low density polyethylene or a thin film of nylon directly onto a finely apertured, macroscopically expanded, three-dimensional web 20' of the type generally disclosed in FIG. 2A. A suitable material and process for producing a web such as 20' is generally disclosed in Example 1 of the commonly assigned, co-pending U.S. Patent Application of John J. Curro, James C. Baird, Donald L. Gerth, George M. Vernon and E. Kelly Linman entitled MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES, Ser. No. 740,145, issued on Sept. 2, 1986 as U.S. Pat. No. 4,609,518, and incorporated herein by reference. The resultant composite structure 19' would exhibit a liquid impervious barrier layer 25 comprised of the thin polyethylene or Nylon coating and a non-occulsive, finely apertured and macroscopically expanded wearer contacting layer 20'.

Still another approach might be to kiss coat a suitable monomer or other suitable crosslinkable coating onto the surface of a web such as 20' and thereafter cure the monomer in place using a known curing stimulus, such as an electron beam or an ultraviolet light.

While particular embodiments of the present invention has been illustrated and described, it will be obvious to those skilled in the art that various changes and modifications can be made without departing from the spirit and scope of the invention, and it is intended to cover in the appended claims all such modifications that are within the scope of this invention

What is claimed is:

1. A composite backsheet for use adjacent an absorbent device, said backsheet comprising:
    (a) a first innermost substantially liquid-impervious layer juxtaposed adjacent said absorbent device, said liquid-impervious layer being soft and compliant, whereby it is resistant to noise under conditions of movement relative to the wearer's body; and
    (b) a second outermost layer comprising a liquid-pervious polymeric film secured in superposed relation adjacent said innermost layer, said polymeric film exhibiting a multiplicity of resilient protuberances across its exposed surface, each protuberance originating in a plane adjacent said innermost layer and protruding outwardly, each protuberance terminating to form a volcano-like aperture at its apex, each of said volcano-like apertures exhibiting a multiplicity of outwardly oriented cusps which contact the wearer's skin in use to prevent said polymeric film from sticking to the wearer's skin, said protuberances further permitting air circulation between said innermost layer and said outermost layer, whereby the wearer's skin remains substantially non-occluded by said composite backsheet at points of contact between said backsheet and the wearer's skin.

2. The composite backsheet of claim 1 wherein said second outermost layer is macroscopically expanded to provide a multiplicity of macroscopic cross-section three-dimensional debossments in its surface, the endwalls of said debossments being positioned adjacent said first innermost substantially liquid-impervious layer.

3. The composite backsheet of claim 2, wherein said endwalls of said debossments in said second outermost layer comprising said polymeric film include macroscopic cross-section apertures.

4. The composite backsheet of claim 1, wherein said first innermost substantially liquid-impervious layer and said second outermost liquid-pervious layer are secured directly to one another.

5. The composite backsheet of claim 4, wherein said first innermost substantially liquid-impervious layer comprises a substantially continuous polymeric coating applied to the non-wearer contacting surface of said second outermost layer comprising said polymeric film.

6. The composite backsheet of claim 1, wherein said first innermost substantially liquid impervious layer comprises a low modulus polymer which has been cured in place.

7. The composite backsheet of claim 1, wherein said first innermost substantially liquid-impervious layer is vapor-pervious.

8. The composite backsheet of claim 2, wherein the density of said protuberances in said second outermost layer comprising said polymeric film is at least about 80 per inch by about 80 per inch, as measured in the non-debossed areas of said web.

9. The composite backsheet of claim 8, wherein said protuberances are regularly spaced with respect to one another.

10. The composite backsheet of claim 8, wherein substantially all of said protuberances are of substantially the same size and shape.

11. A composite backsheet for use adjacent an absorbent device, said backsheet comprising:
(a) a first innermost substantially liquid-impervious layer juxtaposed adjacent said absorbent device, said liquid-impervious layer being soft and compliant, whereby it is resistant to noise under conditions of movement relative to the wearer's body; and
(b) a second outermost layer comprising a liquid-pervious polymeric film secured to said innermost layer, said polymeric film exhibiting a multiplicity of resilient protuberances across its exposed surface, the density of said protuberances being at least about 80 per inch by about 80 per inch, each protuberance originating in a plane adjacent said innermost layer and protruding outwardly, each protuberance terminating to form a volcano-like aperture at its apex, each of said volcano-like apertures exhibiting a multiplicity of outwardly oriented cusps which contact the wearer's skin in use to prevent said polymeric film from sticking to the wearer's skin, said protuberances further permitting air circulation between said innermost layer and said outermost layer, whereby the wearer's skin remains substantially non-occluded by said composite backsheet at points of contact between said backsheet and the wearer's skin.

12. The composite backsheet of claim 11 wherein said second outermost layer is macroscopically expanded to provide a multiplicity of macroscopic cross-section three-dimensional debossments in its surface, the endwalls of said debossments being positioned adjacent said first innermost substantially liquid-impervious layer.

13. The composite backsheet of claim 11, wherein said endwalls of said debossments in said second outermost layer comprising said polymeric film include macroscopic cross-section apertures.

14. The composite backsheet of claim 11, wherein said substantially liquid-impervious layer is vapor-pervious.

15. The composite backsheet of claim 11, wherein said protuberances are regularly spaced with respect to one another.

16. The web composite backsheet of claim 11, wherein substantially all of said protuberances are of substantially the same size and shape.

17. An absorbent device comprising:
(a) a liquid-pervious wearer contacting topsheet;
(b) a liquid absorbent element secured beneath said liquid-pervious topsheet; and
(c) a composite backsheet secured adjacent the surface of said absorbent element opposite said topsheet, said backsheet comprising a first innermost substantially liquid-impervious layer juxtaposed adjacent said absorbent device, said liquid-impervious layer being soft and compliant, whereby it is resistant to noise under conditions of movement relative to the wearer's body, and a second outermost layer comprising a liquid-pervious polymeric film secured to said first innermost layer, said polymeric film exhibiting a multiplicity of resilient protuberances across its exposed surface, the density of said protuberances being at least about 80 per inch by about 80 per inch, each protuberance originating in a plane adjacent said first innermost layer and protruding outwardly, each protuberance terminating to form a volcano-like aperture at its apex, each of said volcano-like apertures exhibiting a multiplicity of outwardly oriented cusps which contact the wearer's skin in use to prevent said polymeric film from sticking to the wearer's skin, said protuberances further permitting air circulation between said innermost layer and said outermost layer, whereby the wearer's skin remains substantially non-occluded by said composite backsheet at points of contact between said backsheet and the wearer's skin.

18. The absorbent device of claim 17, wherein said composite backsheet overlies at least a portion of said wearer contacting topsheet.

* * * * *

UNITED STATES PATENT AND TRADEMARK OFFICE
CERTIFICATE OF CORRECTION

PATENT NO. : 4,681,793

DATED : July 21, 1987

INVENTOR(S) : E. Kelly Linman, John J. Curro, Eugene Weinshenker

It is certified that error appears in the above-identified patent and that said Letters Patent is hereby corrected as shown below:

Column 1, line 24, "," should read -- . --.

Column 3, line 19, "dependant" should read -- dependent --.

Column 6, line 37, "polytetrafluorethylene" should read -- polytetrafluoroethylene --.

Column 10, line 23, "has" should read -- have --.

Column 10, line 28, after "invention" insert -- . --.

Column 12, line 17, delete "web".

Signed and Sealed this

Tenth Day of November, 1987

Attest:

DONALD J. QUIGG

Attesting Officer

Commissioner of Patents and Trademarks